US00PP27323P2

(12) United States Plant Patent
NeSmith

(10) Patent No.: US PP27,323 P2
(45) Date of Patent: Nov. 1, 2016

(54) SOUTHERN HIGHBUSH BLUEBERRY PLANT NAMED 'TH-948'

(50) Latin Name: *Vaccinium corymbosum*
Varietal Denomination: TH-948

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/545,952

(22) Filed: Jul. 10, 2015

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — Annette Para
(74) *Attorney, Agent, or Firm* — Klarquist Sparkman, LLP

(57) ABSTRACT

The new variety 'TH-948' is provided. The new and distinct variety ripens around early May in southern Georgia and mid May in middle Georgia. The fruit of the new variety 'TH-948' are large, firm, have good flavor and scar. The new variety 'TH-948' is vigorous with an estimated chilling requirement of about 500 to 550 hours at or below approximately 7° C. The asexually reproduced variety is reliably propagated vegetatively.

5 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TH-948' is a southern highbush blueberry plant that is a *Vaccinium corymbosum.*

Variety denomination: The new southern highbush blueberry plant claimed is of the variety denominated 'TH-948'.

BACKGROUND OF THE INVENTION

The present invention relates to the discovery of a new and distinct cultivar of southern highbush blueberry plant botanically known as a *Vaccinium corymbosum* and herein referred to as 'TH-948', as herein described and illustrated.

The new blueberry plant variety 'TH-948' was selected in Griffin, Ga., in 2005. The new variety 'TH-948' ripens around early May in southern Georgia. The fruit of the new variety 'TH-948' have excellent berry size as well as good scar, color, firmness, and flavor. The new variety 'TH-948' has good plant vigor with an estimated chilling requirement of about 500-550 hours at or below 7° C.

Pedigree and history: 'TH-948' was selected in 2005 at the Georgia Experiment Station in Griffin, Ga., originating from a cross of 'Camellia'×'Reveille' made by Dr. D. Scott NeSmith in 2002. The maternal parent, 'Camellia', is a UGA release (U.S. Plant Pat. No. 18,151). The paternal parent, 'Reveille', is a non-patented North Carolina released variety. The selection has been tested in asexually propagated (by vegetative cuttings) plantings at UGA Blueberry Research Farms in Alapaha and Griffin, Ga., since 2007.

SUMMARY OF THE INVENTION

The new blueberry plant variety 'TH-948' has not been observed under all possible environmental conditions. The phenotype may vary somewhat with variations in environment and cultural practices such as temperature and light intensity without, however, any variance in genotype.

The following traits have been repeatedly observed in Alapaha and Griffin, Ga., and are determined to be unique firmly fixed characteristics of the new blueberry plant variety 'TH-948':

1. Excellent berry size;
2. Short fruit development period;
3. Good fruit flavor characteristics;
4. Good fruit firmness.

The new variety 'TH-948' can be compared to the southern highbush blueberry varieties 'Star' (the subject of U.S. Plant Pat. No. 10,675) and 'Camellia' (the subject of U.S. Plant Pat. No. 18,151).

Comparison: The 'TH-948' plant flowers 2 weeks after 'Star' and ripens within a few days of 'Star' in the early Georgia southern highbush season. 'TH-948' has large, firm berries with good flavor and scar as compared to standards 'Star' and 'Camellia' in Alapaha and Griffin, Ga. over a 5-year period (Tables 1 and 2). Table 3 describes yield, berry weight, firmness and Brix for 'TH-948' as compared to the 'Star' and 'Camellia' southern highbush blueberry cultivars, for the years 2010-2013. 'TH-948' had average berry weight that is greater than 'Star' and comparable to 'Camellia'. Major attractions of 'TH-948' are its excellent berry size and very short fruit development period. 'TH-948' is able to provide high quality fruit during early May in southern Georgia while minimizing frost/freeze protection expenses. Preliminary studies suggest that 'TH-948' is suitable for high density planting and is also likely suitable for machine harvesting.

TABLE 1

5-year average ratings of some fruit and plant characteristics of 'TH-948' and southern highbush standard cultivars 'Star' and 'Camellia' from 2009-2013 in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in Fall 2007.

| | Alapaha location | | |
|---|---|---|---|
| Berry and plant attributes[1/] | 'Star' | 'Camellia' | 'TH-948' |
| Berry size | 7.6 ± 0.2 | 8.9 ± 0.2 | 8.4 ± 0.2 |
| Berry scar | 7.0 ± 0.1 | 7.2 ± 0.2 | 7.4 ± 0.1 |
| Berry color | 7.1 ± 0.1 | 8.7 ± 0.2 | 7.8 ± 0.1 |
| Berry firmness | 7.2 ± 0.1 | 7.2 ± 0.1 | 7.8 ± 0.2 |
| Berry flavor | 7.0 ± 0.1 | 7.8 ± 0.1 | 7.8 ± 0.2 |
| Cropping | 4.7 ± 1.7 | 5.4 ± 0.3 | 5.2 ± 0.5 |
| Plant vigor | 6.3 ± 0.2 | 9.8 ± 0.2 | 7.6 ± 0.4 |
| Date of 50% flowering | March 3 | March 11 | March 17 |
| Date of 50% ripening | May 8 | May 15 | May 11 |
| Fruit development period (days) | 66.3 ± 6.1 | 65.3 ± 4.9 | 55.0 ± 5.2 |

[1/]Values are means ± the standard error with n = 5.

TABLE 2

5-year average ratings of some fruit and plant characteristics of 'TH-948' and southern highbush standard cultivars 'Star' and 'Camellia' (2009-2013) in field test plots at Griffin, GA. Rating scales are based on a 1 to 10 score, with 1 being the least desirable and 10 being the most desirable. A value of 6-7 is generally considered to be the minimum acceptable rating for a commercial cultivar. These plants were established in Fall 2007.

| | Griffin location | | |
|---|---|---|---|
| Berry and plant attributes[1/] | 'Star' | 'Camellia' | 'TH-948' |
| Berry size | 7.4 ± 0.2 | 8.6 ± 0.2 | 8.7 ± 0.2 |
| Berry scar | 6.9 ± 0.1 | 7.0 ± 0.1 | 7.2 ± 0.1 |
| Berry color | 7.1 ± 0.1 | 7.9 ± 0.2 | 7.3 ± 0.2 |
| Berry firmness | 7.2 ± 0.1 | 7.2 ± 0.1 | 7.7 ± 0.3 |
| Berry flavor | 7.1 ± 0.1 | 7.4 ± 0.2 | 7.4 ± 0.2 |
| Cropping | 6.8 ± 1.1 | 7.9 ± 0.2 | 6.2 ± 0.2 |
| Plant vigor | 8.5 ± 0.3 | 9.8 ± 0.1 | 9.1 ± 0.2 |
| Date of 50% flowering | March 13 | March 25 | March 28 |
| Date of 50% ripening | May 25 | May 31 | May 21 |
| Fruit development period (days) | 73.3 ± 10.4 | 67.3 ± 4.8 | 54 ± 2.3 |

[1/]Values are means ± the standard error with n = 5.

TABLE 3

Yield, and berry weight, firmness, and Brix for 'Star' and 'Camellia' cultivars and 'TH-948' grown in Griffin, GA during 2010-2013.

| Year | 'Star' | 'Camellia' | 'TH-948' |
|---|---|---|---|
| | Yield (lbs/bush)[1/] | | |
| 2011 | 12.7 ± 3.6 | 9.7 ± 0.9 | 8.5 ± 1.2 |
| 2012 | 11.7 ± 2.3 | 10.5 ± 0.8 | 7.2 ± 0.7 |
| 2013 | 3.9 ± 0.6 | 15.9 ± 1.0 | 7.3 ± 0.6 |
| Avg | 9.4 | 12.0 | 7.7 |
| | Berry wt. (g/berry)[2/] | | |
| 2010 | 1.53 ± 0.09 | 2.94 ± 0.12 | 3.15 ± 0.05 |
| 2011 | 1.20 ± 0.04 | 1.97 ± 0.11 | 2.08 ± 0.10 |
| 2012 | 1.80 ± 0.07 | 1.60 ± 0.09 | 2.17 ± 0.15 |
| 2013 | 1.79 ± 0.06 | 2.56 ± 0.10 | 2.12 ± 0.21 |
| Avg | 1.58 | 2.28 | 2.38 |
| | Firmness (g/mm)[2/] | | |
| 2010 | 196 ± 4 | 150 ± 2 | 165 ± 1 |
| 2011 | 206 ± 6 | 166 ± 3 | 188 ± 5 |

TABLE 3-continued

Yield, and berry weight, firmness, and Brix for 'Star' and 'Camellia' cultivars and 'TH-948' grown in Griffin, GA during 2010-2013.

| Year | 'Star' | 'Camellia' | 'TH-948' |
|---|---|---|---|
| 2012 | 190 ± 5 | 164 ± 4 | 186 ± 7 |
| 2013 | 191 ± 5 | 150 ± 2 | 188 ± 9 |
| Avg | 196 | 157 | 182 |
| | Brix (%)[3/] | | |
| 2012 | 13.9 ± 0.6 | 14.5 ± 0.4 | 12.0 ± 0.2 |
| 2013 | 13.5 ± 0.5 | 13.3 ± 0.3 | 12.3 ± 0.3 |
| Avg | 13.7 | 13.9 | 12.2 |

[1/]Values are means ± the standard error with n = 3.
[2/]Values are means ± the standard error with n = 3 (each sample derived from 25 berry avg).
[3/]Values are means ± the standard error with n = 3 (each sample derived from 5 berry composite).

BRIEF DESCRIPTION OF THE FIGURES

The accompanying photographic illustrations show typical specimens in full color of the foliage, flowering, and fruit of the new variety 'TH-948'. The colors are as nearly true as is reasonably possible in a color representation of this type.

BOTANICAL DESCRIPTION

Figure 1:
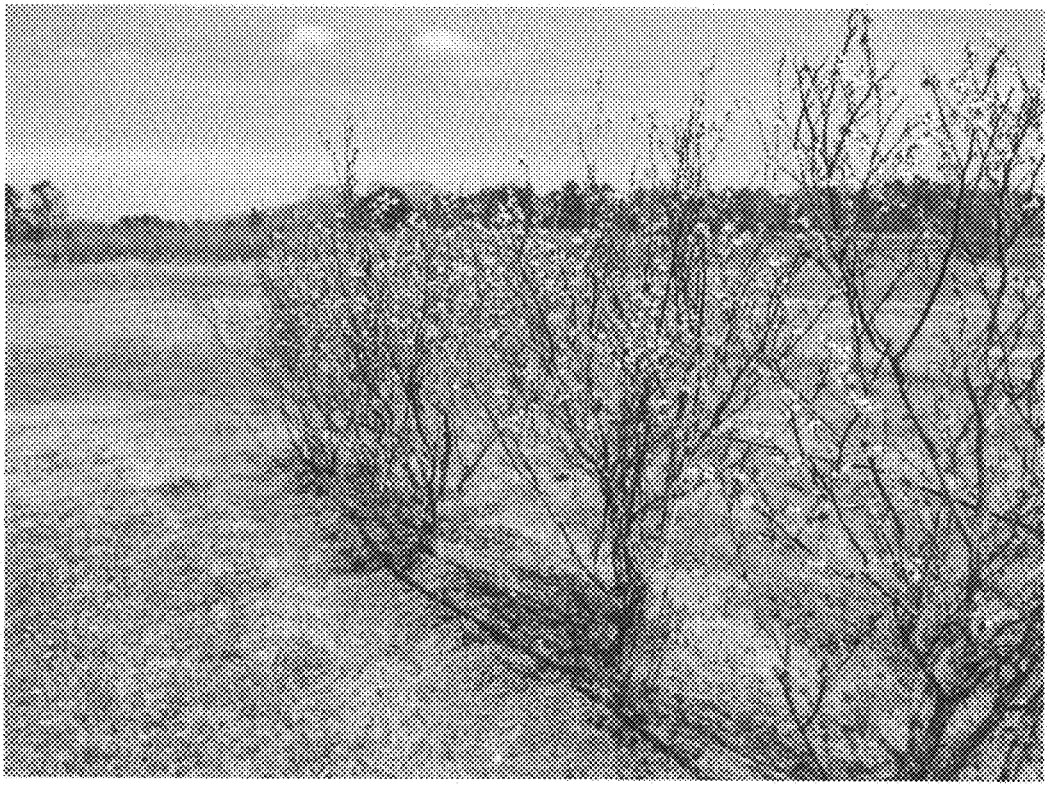
FIG. 1 is a photograph of the new variety 'TH-948' during flowering in Griffin, Ga.
Figure 2:
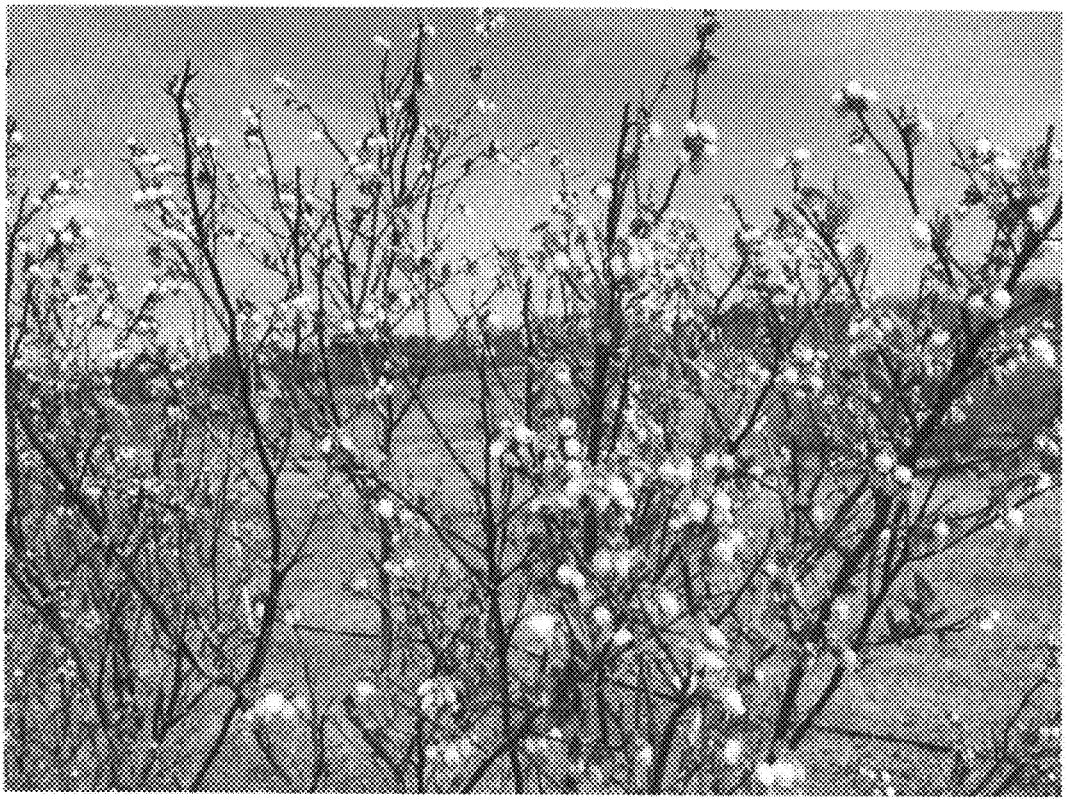
FIG. 2 is a close up photograph of the new variety 'TH-948' during flowering in Griffin, Ga.
Figure 3:
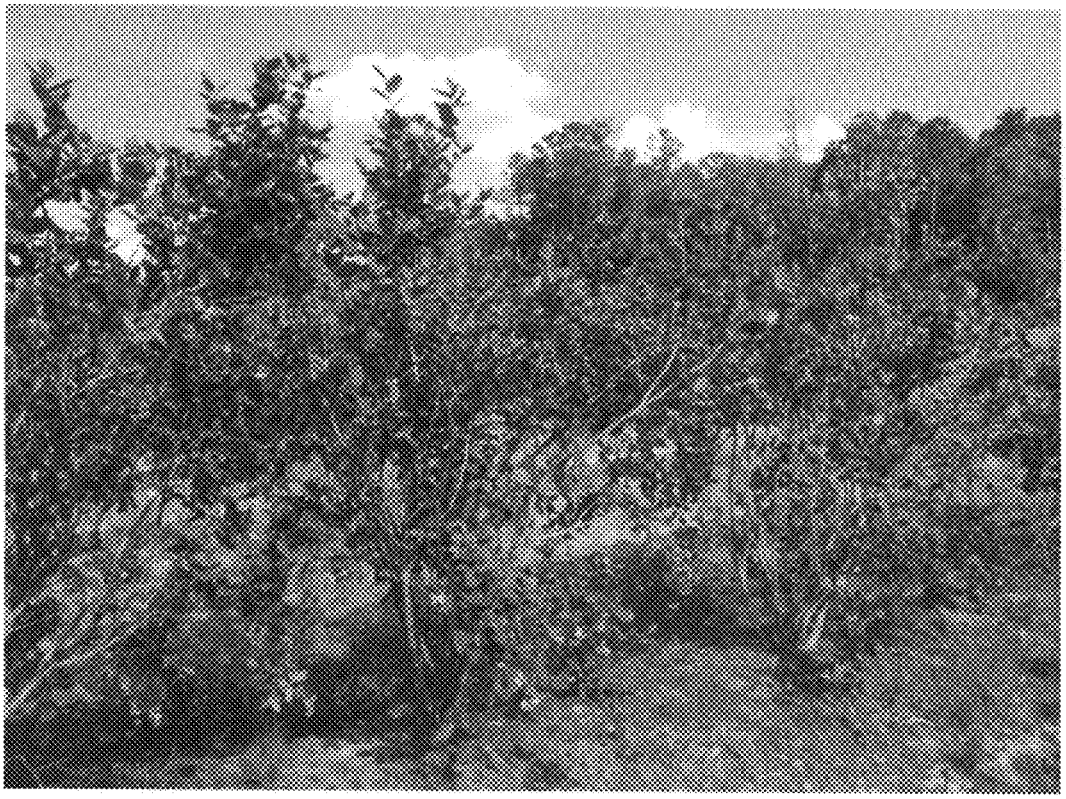
FIG. 3 is a photograph of new variety 'TH-948' during fruit ripening in Griffin, Ga.
Figure 4:
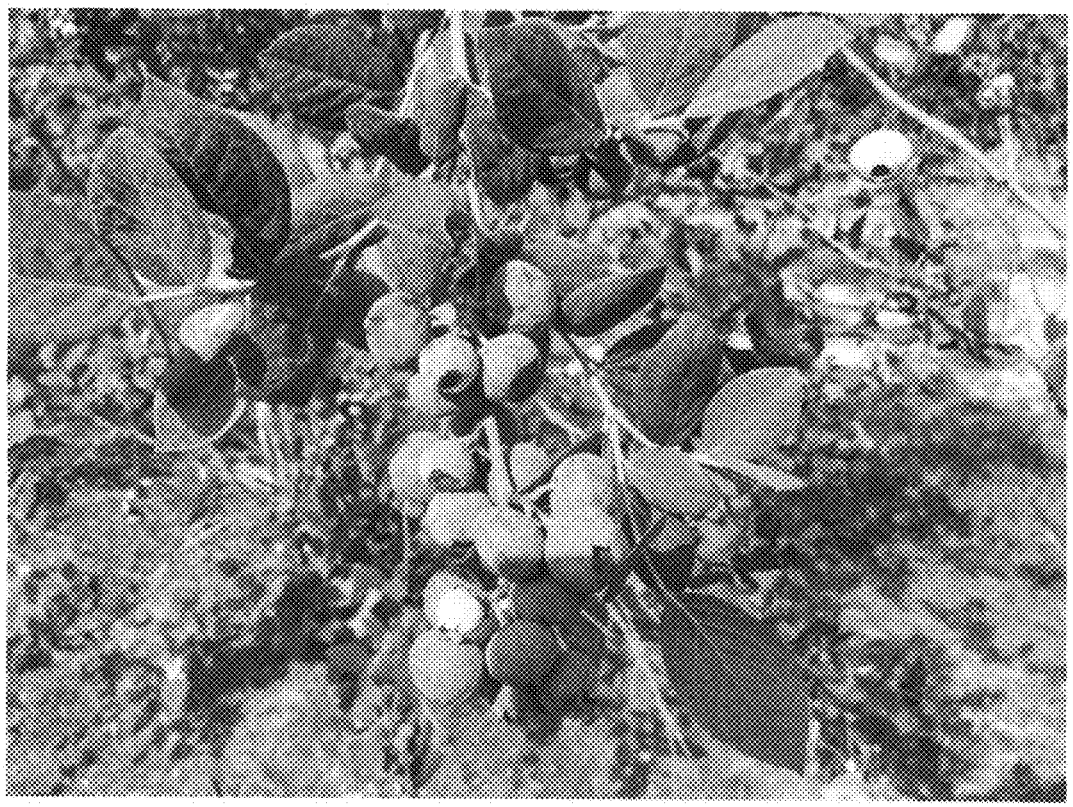
FIG. 4 is a close up photograph of the new variety 'TH-948' fruit clusters.
Figure 5:
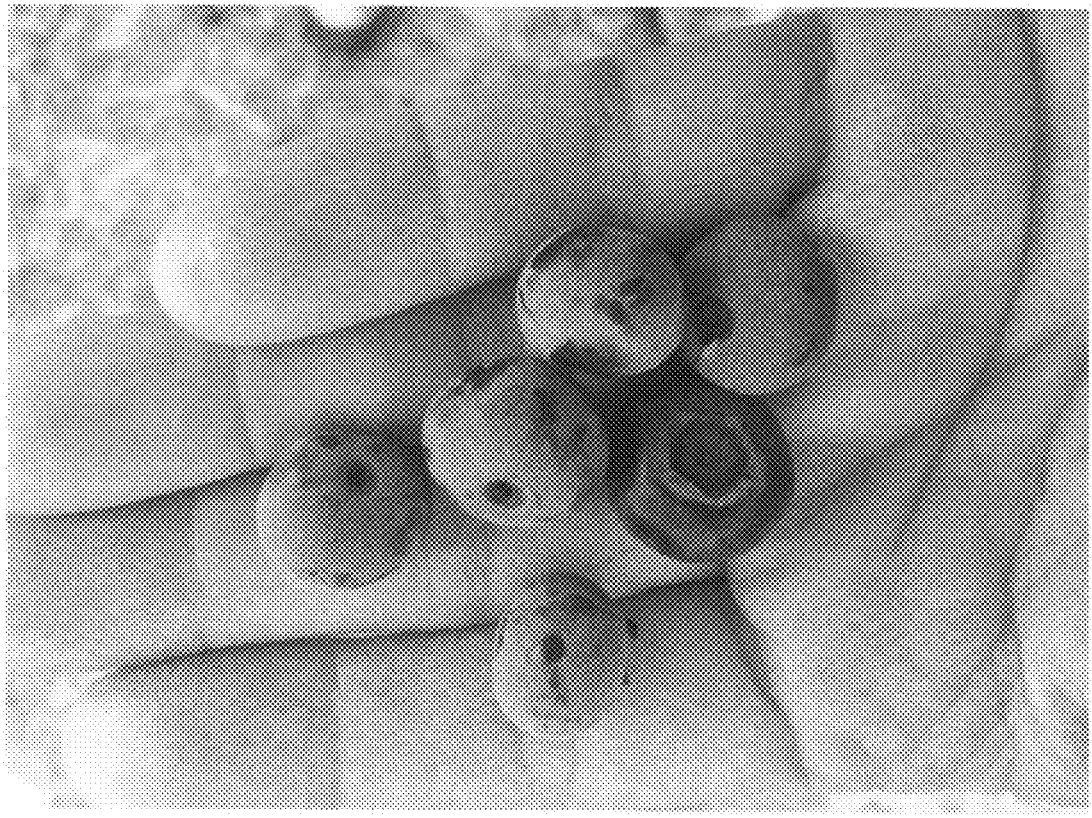
FIG. 5 is a close up photograph of typical fruit of the new variety 'TH-948'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following is a detailed description of the botanical and pomological characteristics of the new variety 'TH-948'. Where dimensions, sizes, colors, and other characteristics are given, it is to be understood that such characteristics are approximations and averages set forth as accurately as practicable. The descriptions reported herein are largely from specimen plants grown in Alapaha and Griffin, Ga., with supplemental irrigation. Plants were about 3 to about 6 years old.

PLANT

Size: 1.9 to 2.2 m tall by about 4 years of age. Plants grown under highly productive soil and fertility conditions have exceeded 2.2 m tall in 4 years. The plant crown, or base, is narrow, typically 10 to 20 cm in diameter. Upper portion of plant canopy reaches 1.1 to 1.3 m in diameter by 3 to 4 years.

Growth habit: Strongly upright, with 1 to 4 main canes arising from the crown, and multiple branching of shoots (2 to 3 per cane) from those canes at 25 to 40 cm above the soil surface.

Growth: Highly vigorous.

Productivity: Moderate to good crop and yield, averaging 7 to 10 lbs of fruit per plant each year for plants 4 years and older grown under well fertilized and irrigated field conditions.

Hardiness: Similar to other southern highbush cultivars such as 'Star' (U.S. Plant Pat. No. 10,675) and 'Camellia' (U.S. Plant Pat. No. 18,151).

Chilling requirement: 500-550 hours of temperatures at or below 7° C. (about 45° F.) to induce normal leafing and flowering during the spring under conventional production systems. The chill requirement is less than the male parent 'Reveille' (non-patented variety; more than 700 hours of chilling required) but more than the female parent 'Camellia' (U.S. Plant Pat. No. 18,151; estimated 400-450 hours of chilling required).

Leafing: Plants tend to break sufficient leaf buds simultaneously with, or shortly after, anthesis.

Canes:
- *Diameter.*—30 to 50 mm for base of main canes that are about 4 years old and older. 10 to 15 mm in about 2 year old wood. 5 to 10 mm in current season wood.
- *Color.*—Greyed-Green RHS 197B for base of canes that are about 4 years old and older. Greyed-Brown RHS N199C in about 2 year old wood. Yellow-Green RHS 145B in current season wood.

Fruiting wood: Moderate number of twigs 20 to 25 cm in length, with internode lengths of 25-30 mm common.

Disease resistance: No exceptional disease resistance or susceptibility observed; typical for southern highbush 'Star' and 'Camellia' cultivars.

FOLIAGE

Leaf color: Healthy mature leaves.
- *Top side.*—Green RHS 137B.
- *Under side.*—Green RHS 138D.

Leaf arrangement: Alternate, simple.
Leaf shape: Lanceolate to ovate.
Leaf surface: Glaucous.
Leaf margins: Nearly entire, smooth.
Leaf venation: Slightly reticulated.
Leaf apices: Broadly acute.
Leaf bases: Broadly acute.
Leaf dimensions:
- *Length.*—55.0 to 60.0 mm.
- *Width.*—40.0 to 45.0 mm.

Petioles: Small.
- *Length.*—3.0 to 4.0 mm.
- *Width.*—1.5 to 2.0 mm.
- *Color.*—Yellow-Green RHS 145C.

FLOWERS

Date of 50% anthesis: March 17 in southern Georgia and March 28 in middle Georgia (5 year average).
Flower shape: Urceolate.
Flower bud number: Medium, averaging 3 to 6 buds per fruiting shoot.
Flowers per cluster: 4 to 6 common.
Flower fragrance: None.
Corolla:
- *Color.*—White RHS 155C (open flower).
- *Length.*—7.0 to 8.0 mm.
- *Width.*—7.0 to 8.0 mm.
- *Aperture width.*—3.5 to 4.5 mm.

Flower peduncle:
- *Length.*—8.0 to 14.0 mm.
- *Color.*—Green RHS 139D, with streaks of Red-Purple RHS 63A observed under cool weather conditions.

Flower pedicle:
- *Length.*—4.5 to 5.5 mm.
- *Color.*—Green RHS 139D.

Calyx (with sepals):
- *Diameter.*—7.5 to 8.5 mm.
- *Color.*—Green RHS 138B.

Stamen:
- *Length.*—7.0 to 7.5 mm.
- *Number per flower.*—10.
- *Filament color.*—Yellow-Green RHS 145C.

Style:
- *Length.*—7.0 to 7.5 mm.
- *Color.*—Yellow-Green RHS 145B.

Pistil:
- *Length.*—9.0 to 10.5 mm.
- *Ovary color (exterior).*—Green RHS 138B to Green 139C.

Anther:
- *Length.*—4.0 to 4.5 mm.
- *Number.*—10.
- *Color.*—Greyed-Orange RHS N167A.

Pollen:
- *Abundance.*—Medium.
- *Color.*—Yellow-White RHS 158A.

Self-compatibility: The cultivar has a moderate degree of self-compatibility.

FRUIT

Date of 50% maturity: May 11 in southern Georgia and May 21 in middle Georgia (5 year average).
Fruit development period: 52 to 58 days.
Berry color:
- *With wax.*—Violet-Blue RHS 97B.
- *With wax removed.*—Black RHS 202A.

Berry surface wax abundance: Medium to high.
Berry flesh color: Yellow-Green RHS 145C.
Berry weight:
- *First harvest.*—2.0 g to 2.8 g.
- *Second harvest.*—1.7 g to 2.1 g.

Berry size:
- *Height from calyx to scar.*—11.0 to 13.0 mm.
- *Diameter.*—17.0 to 19.0 mm.

Berry shape: Semi-spherical.
Fruit stem scar: Medium, medium-dry, with little or no tearing upon harvest.
Calyx: Depth 2.0 to 3.0 mm; width 7.0 to 10.0 mm; sepals slightly showing and most often turn outward when present.
Berry firmness: Good to very good firmness.
Berry flavor and texture: Very good flavor. Smooth texture.
Storage quality: Good.
Suitability for mechanical harvesting: Likely suitable.
Uses: Primarily to be used as fresh fruit for shipping, for customer pick, and processing markets.

SEED

Seed abundance in fruit: Low to medium, with 10 to 20 fully developed seeds per berry.
Seed color: Greyed-Orange RHS 164B to 165B.
Seed dry weight: 39.0 mg per 100 seeds.
Seed size: 1.3 to 1.9 mm long; 0.3 to 0.5 mm wide for fully developed seeds.

What is claimed is:

1. A new and distinct variety of southern highbush blueberry plant named 'TH-948', substantially as illustrated and described herein.

* * * * *